US009343057B1

(12) United States Patent
Shahmurad et al.

(10) Patent No.: US 9,343,057 B1
(45) Date of Patent: May 17, 2016

(54) SUPPRESSING SUDDEN CABIN NOISE DURING HANDS-FREE AUDIO MICROPHONE USE IN A VEHICLE

(71) Applicants: GM Global Technology Operations LLC, Detroit, MI (US); General Motors LLC, Detroit, MI (US)

(72) Inventors: Bassam S. Shahmurad, Clinton Township, MI (US); MD Foezur Rahman Chowdhury, Troy, MI (US)

(73) Assignees: General Motors LLC, Detroit, MI (US); GM Global Technology Operations LLC, Detroit, MI (US)

( * ) Notice: Subject to any disclaimer, the term of this patent is extended or adjusted under 35 U.S.C. 154(b) by 20 days.

(21) Appl. No.: 14/529,743

(22) Filed: Oct. 31, 2014

(51) Int. Cl.
*G10K 11/16* (2006.01)
*H03B 29/00* (2006.01)
*A61F 11/06* (2006.01)

(52) U.S. Cl.
CPC ........ *G10K 11/16* (2013.01); *G10K 2210/1282* (2013.01)

(58) Field of Classification Search
CPC ....................... G10K 11/16; G10K 2210/1282
USPC ........................................................ 381/71.4
See application file for complete search history.

(56) References Cited

U.S. PATENT DOCUMENTS

2010/0172510 A1* 7/2010 Juvonen ............... G10K 11/178 381/71.6

* cited by examiner

*Primary Examiner* — Paul S Kim
(74) *Attorney, Agent, or Firm* — Christopher DeVries; Reising Ethington P.C.

(57) ABSTRACT

A vehicle audio quality system for suppressing sudden vehicle cabin noise is provided, as well as methods of using the system. The system includes: an arrangement of heterogeneous microphones and a noise cancellation module (NCM). The microphone arrangement includes: a first microphone and a plurality of secondary microphones. The NCM includes a controller and a non-transitory computer-readable medium for storing application software executable by the controller to improve the quality of desired cabin audio received by the first microphone, the software performing the steps of: receiving a desired audio input from the first microphone; receiving supplemental audio input via the plurality of secondary microphones that includes a sudden cabin noise input; and applying a suppression procedure to the sudden cabin noise input.

18 Claims, 5 Drawing Sheets

Figure 3A
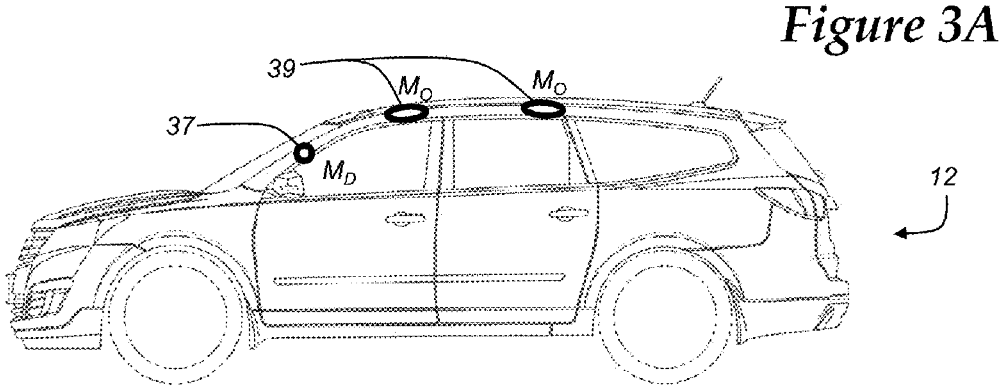
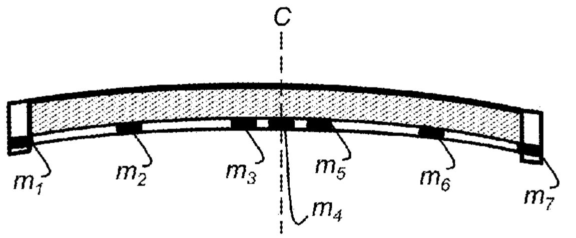
Figure 3B
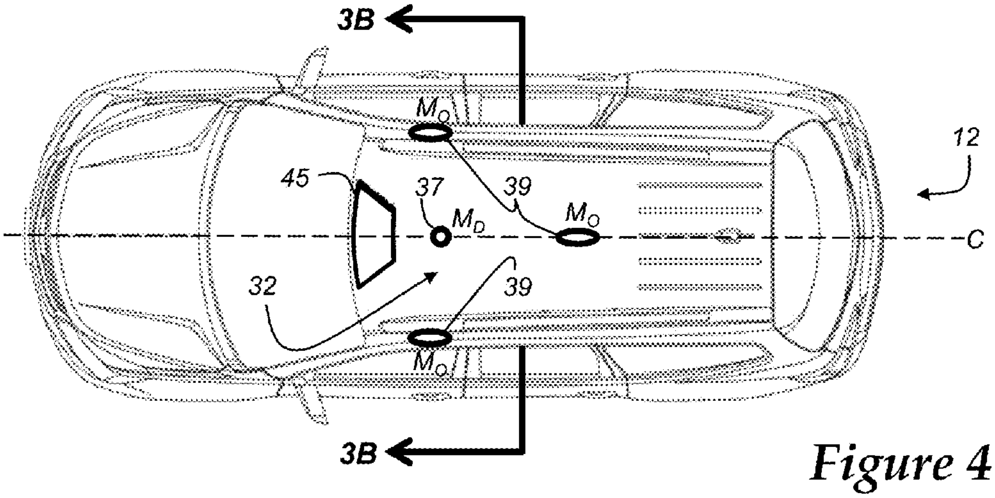
Figure 4

SUPPRESSING SUDDEN CABIN NOISE DURING HANDS-FREE AUDIO MICROPHONE USE IN A VEHICLE

TECHNICAL FIELD

The present invention relates to a hands-free audio system in a vehicle, and more particularly to suppressing sudden cabin noise received by the system.

BACKGROUND

A substantial portion of vehicle cabin noise may derive from wind, tires, and other vehicle mechanical systems such as the engine, suspension, and exhaust. Proper vehicle maintenance and after-market solutions such as sound deadening pads may be used to lessen cabin noise. In general, excessive cabin noise is undesirable or nuisance for vehicle users.

SUMMARY

According to an embodiment of the invention, there is provided a method of sudden cabin noise suppression for a vehicle that includes the steps of: providing an arrangement of heterogeneous microphones in the vehicle, the arrangement including a hands-free audio (HFA) microphone and an array of secondary microphones, wherein the arrangement includes at least one directional microphone and at least one omni-directional microphone; receiving a desired audio input via the HFA microphone; while receiving the desired audio input, receiving supplemental audio inputs via the array of secondary microphones, wherein the supplemental audio inputs include a sudden cabin noise input; applying a first suppression procedure to the sudden cabin noise input; and when the first suppression procedure does not normalize the sudden cabin noise input, then applying a second suppression procedure.

According to another embodiment of the invention, there is provided a method of sudden cabin noise suppression for a vehicle that includes the steps of: providing an arrangement of microphones in the vehicle, the arrangement comprising a hands-free audio (HFA) microphone and an array of active-noise canceling (ANC) microphones; receiving a desired audio input via the HFA microphone; while receiving the desired audio input, receiving supplemental audio inputs via the array of ANC microphones, wherein the supplemental audio inputs include a sudden cabin noise input; applying a first suppression procedure to the sudden cabin noise input; and when the first suppression procedure does not normalize the sudden cabin noise input, then applying a second suppression procedure.

According to another embodiment of the invention, there is provided a vehicle audio quality system for suppressing sudden vehicle cabin noise. The system includes: an arrangement of heterogeneous microphones and a noise cancellation module (NCM). The microphone arrangement includes: a first microphone and a plurality of secondary microphones. The NCM includes a controller and a non-transitory computer-readable medium for storing application software executable by the controller to improve the quality of desired cabin audio received by the first microphone, the software performing the steps of: receiving a desired audio input from the first microphone; receiving supplemental audio input via the plurality of secondary microphones that includes a sudden cabin noise input; and applying a suppression procedure to the sudden cabin noise input.

BRIEF DESCRIPTION OF THE DRAWINGS

One or more embodiments of the invention will hereinafter be described in conjunction with the appended drawings, wherein like designations denote like elements, and wherein:

FIG. 3A is an elevation view of a vehicle also shown in FIGS. 4-9;

FIG. 3B is a partial sectional view of a vehicle roof and headliner along section lines 4-4 of FIG. 4;

FIGS. 4-9 are schematic plan views of various microphone arrangements; and

DETAILED DESCRIPTION OF THE ILLUSTRATED EMBODIMENT(S)

The system and methods described below pertain to a hands-free audio system in a vehicle with which vehicle users typically place and receive mobile telephone calls. More specifically, the system described herein is configured to receive sudden cabin noise during a call and suppress the sudden noise so that when the audio signal is wirelessly transmitted to the person on the other end of the call, the sudden cabin noise is adequately attenuated or dampened. As will be described below, it is desirable to normalize the sudden cabin noise with any other noise inputs to achieve this adequate attenuation. Unlike conventional systems, the system described below achieves this attenuation with an arrangement of heterogeneous microphones; i.e., microphones of different types. In addition, the methods described herein provide an isolation technique that enables one or more audio channels associated with receiving the loudest portion of the sudden cabin noise to be temporarily canceled, if necessary.

Communications System—

Figure 1:
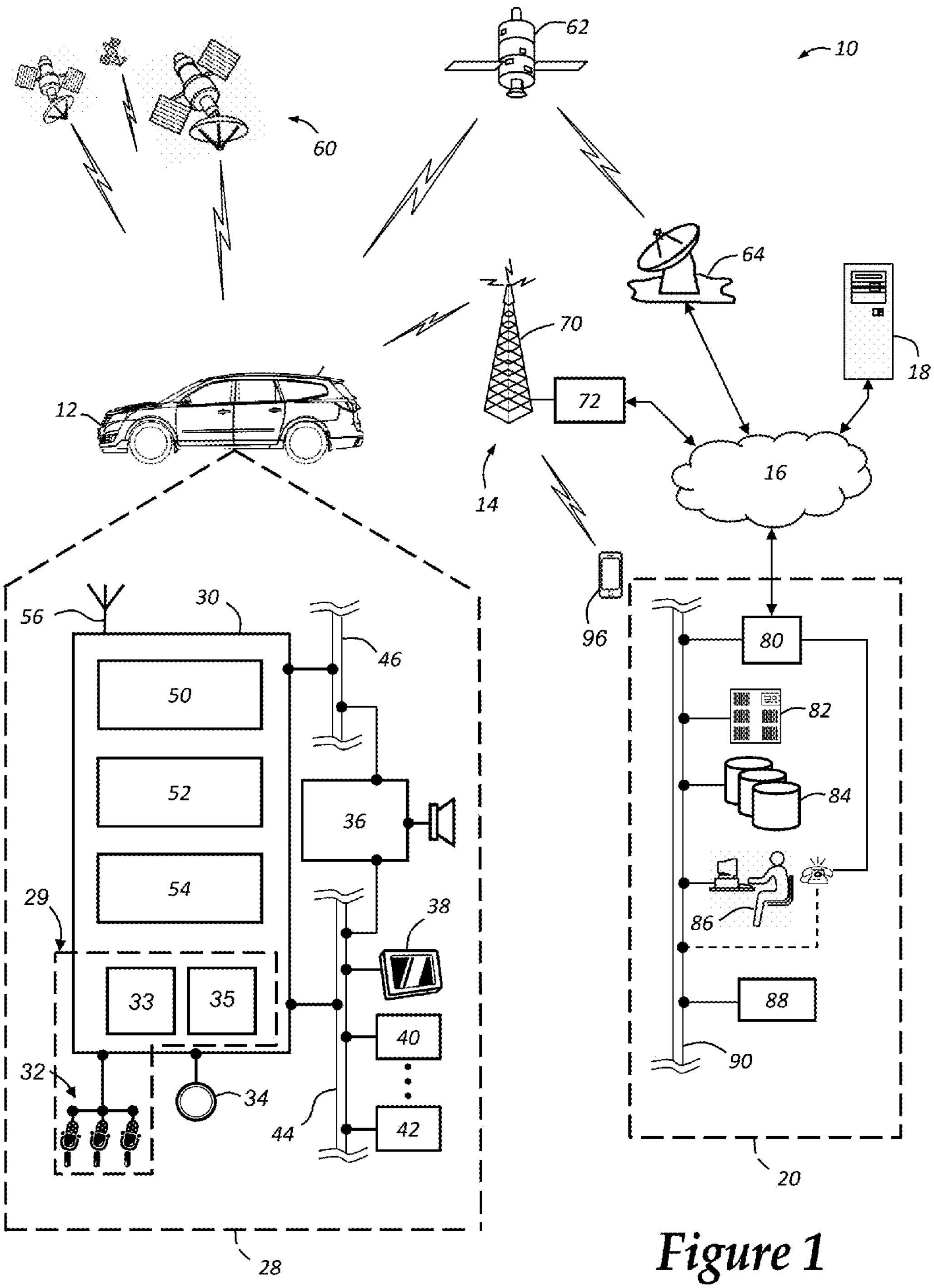
FIG. 1 is a block diagram depicting an embodiment of a communications system that is capable of utilizing the method disclosed herein.

With reference to FIG. 1, there is shown an operating environment that comprises a mobile vehicle communications system 10 and that can be used to implement the method disclosed herein. Communications system 10 generally includes a vehicle 12, one or more wireless carrier systems 14, a land communications network 16, a computer 18, and a call center 20. It should be understood that the disclosed method can be used with any number of different systems and is not specifically limited to the operating environment shown here. Also, the architecture, construction, setup, and operation of the system 10 and its individual components are generally known in the art. Thus, the following paragraphs simply provide a brief overview of one such communications system 10; however, other systems not shown here could employ the disclosed method as well.

Vehicle 12 is depicted in the illustrated embodiment as a passenger car, but it should be appreciated that any other vehicle including trucks, sports utility vehicles (SUVs), recreational vehicles (RVs), marine vessels, aircraft, etc., can also be used. Some of the vehicle electronics 28 is shown generally in FIG. 1 and includes a telematics unit 30, a microphone 32, one or more pushbuttons or other control inputs 34, an audio system 36, a visual display 38, and a GPS module 40 as well as a number of vehicle system modules (VSMs) 42. Some of these devices can be connected directly to the telematics unit such as, for example, the microphone 32 and pushbutton(s) 34, whereas others are indirectly connected using one or more network connections, such as a communications bus 44 or an entertainment bus 46. Examples of suitable network connections include a controller area network (CAN), a media oriented system transfer (MOST), a local interconnection network (LIN), a local area network (LAN), and other appropriate connections such as Ethernet or others that conform with known ISO, SAE and IEEE standards and specifications, to name but a few.

Telematics unit 30 can be an OEM-installed (embedded) or aftermarket device that is installed in the vehicle and that enables wireless voice and/or data communication over wireless carrier system 14 and via wireless networking. This enables the vehicle to communicate with call center 20, other telematics-enabled vehicles, or some other entity or device. The telematics unit preferably uses radio transmissions to establish a communications channel (a voice channel and/or a data channel) with wireless carrier system 14 so that voice and/or data transmissions can be sent and received over the channel. By providing both voice and data communication, telematics unit 30 enables the vehicle to offer a number of different services including those related to navigation, telephony, emergency assistance, diagnostics, infotainment, etc. Data can be sent either via a data connection, such as via packet data transmission over a data channel, or via a voice channel using techniques known in the art. For combined services that involve both voice communication (e.g., with a live advisor or voice response unit at the call center 20) and data communication (e.g., to provide GPS location data or vehicle diagnostic data to the call center 20), the system can utilize a single call over a voice channel and switch as needed between voice and data transmission over the voice channel, and this can be done using techniques known to those skilled in the art.

According to one embodiment, telematics unit 30 utilizes cellular communication according to either GSM or CDMA standards and thus includes a standard cellular chipset 50 for voice communications like hands-free calling, a wireless modem for data transmission, an electronic processing device 52, one or more digital memory devices 54, and a dual antenna 56. It will be appreciated that GSM or CDMA standards illustrate merely exemplary implementations and other standards are also possible (e.g., LTE). It should be appreciated that the modem can either be implemented through software that is stored in the telematics unit and is executed by processor 52, or it can be a separate hardware component located internal or external to telematics unit 30. The modem can operate using any number of different standards or protocols such as EVDO, CDMA, GPRS, EDGE, and LTE. When used for packet-switched data communication such as TCP/IP, the telematics unit can be configured with a static IP address or can set up to automatically receive an assigned IP address from another device on the network such as a router or from a network address server.

Wireless networking between the vehicle and other networked devices can also be carried out using telematics unit 30. For this purpose, telematics unit 30 can be configured to communicate wirelessly according to one or more suitable wireless protocols. Examples of wireless network(s) include both cellular networks (as previously described) but also short range wireless communication (SRWC). SRWC is intended to be construed broadly and may include one or more suitable wireless protocols including: any Wi-Fi standard (e.g., IEEE 802.11); Wi-Fi Direct, Bluetooth, or other suitable peer-to-peer standard; wireless infrared transmission; WiMAX; ZigBee™; and/or various combinations thereof. This list is merely meant to provide examples and is not intended to be limiting.

Processor 52 can be any type of device capable of processing electronic instructions including microprocessors, microcontrollers, host processors, controllers, vehicle communication processors, and application specific integrated circuits (ASICs). It can be a dedicated processor used only for telematics unit 30 or can be shared with other vehicle systems. Processor 52 executes various types of digitally-stored instructions, such as software or firmware programs stored in memory 54, which enable the telematics unit to provide a wide variety of services. For instance, processor 52 can execute programs or process data to carry out at least a part of the method discussed herein.

Telematics unit 30 can be used to provide a diverse range of vehicle services that involve wireless communication to and/or from the vehicle. Such services include: turn-by-turn directions and other navigation-related services that are provided in conjunction with the GPS-based vehicle navigation module 40; airbag deployment notification and other emergency or roadside assistance-related services that are provided in connection with one or more collision sensor interface modules such as a body control module (not shown); diagnostic reporting using one or more diagnostic modules; and infotainment-related services where music, webpages, movies, television programs, videogames and/or other information is downloaded by an infotainment module (not shown) and is stored for current or later playback. The above-listed services are by no means an exhaustive list of all of the capabilities of telematics unit 30, but are simply an enumeration of some of the services that the telematics unit is capable of offering. Furthermore, it should be understood that at least some of the aforementioned modules could be implemented in the form of software instructions saved internal or external to telematics unit 30, they could be hardware components located internal or external to telematics unit 30, or they could be integrated and/or shared with each other or with other systems located throughout the vehicle, to cite but a few possibilities. In the event that the modules are implemented as VSMs 42 located external to telematics unit 30, they could utilize vehicle bus 44 to exchange data and commands with the telematics unit.

GPS module 40 receives radio signals from a constellation 60 of GPS satellites. From these signals, the module 40 can determine vehicle position that is used for providing navigation and other position-related services to the vehicle driver. Navigation information can be presented on the display 38 (or other display within the vehicle) or can be presented verbally such as is done when supplying turn-by-turn navigation. The navigation services can be provided using a dedicated in-vehicle navigation module (which can be part of GPS module 40), or some or all navigation services can be done via telematics unit 30, wherein the position information is sent to a remote location for purposes of providing the vehicle with navigation maps, map annotations (points of interest, restaurants, etc.), route calculations, and the like. The position information can be supplied to call center 20 or other remote computer system, such as computer 18, for other purposes, such as fleet management. Also, new or updated map data can be downloaded to the GPS module 40 from the call center 20 via the telematics unit 30.

Apart from the audio system 36 and GPS module 40, the vehicle 12 can include other vehicle system modules (VSMs) 42 in the form of electronic hardware components that are located throughout the vehicle and typically receive input from one or more sensors and use the sensed input to perform diagnostic, monitoring, control, reporting and/or other functions. Each of the VSMs 42 is preferably connected by communications bus 44 to the other VSMs, as well as to the telematics unit 30, and can be programmed to run vehicle system and subsystem diagnostic tests. As examples, one VSM 42 can be an engine control module (ECM) that controls various aspects of engine operation such as fuel ignition and ignition timing, another VSM 42 can be a powertrain control module that regulates operation of one or more components of the vehicle powertrain, and another VSM 42 can be a body control module that governs various electrical components located throughout the vehicle, like the vehicle's power door locks and headlights. According to one embodiment, the engine control module is equipped with on-board diagnostic (OBD) features that provide myriad real-time data, such as that received from various sensors including vehicle emissions sensors, and provide a standardized series of diagnostic trouble codes (DTCs) that allow a technician to rapidly identify and remedy malfunctions within the vehicle. As is appreciated by those skilled in the art, the above-mentioned VSMs are only examples of some of the modules that may be used in vehicle 12, as numerous others are also possible.

Vehicle electronics 28 also includes a number of vehicle user interfaces that provide vehicle occupants with a means of providing and/or receiving information, including a vehicle audio quality system (VAQS) 29 that includes, among other things, an arrangement of microphones 32, pushbuttons(s) 34, audio system 36, and visual display 38. As used herein, the term 'vehicle user interface' broadly includes any suitable form of electronic device, including both hardware and software components, which is located on the vehicle and enables a vehicle user to communicate with or through a component of the vehicle.

Figure 2:
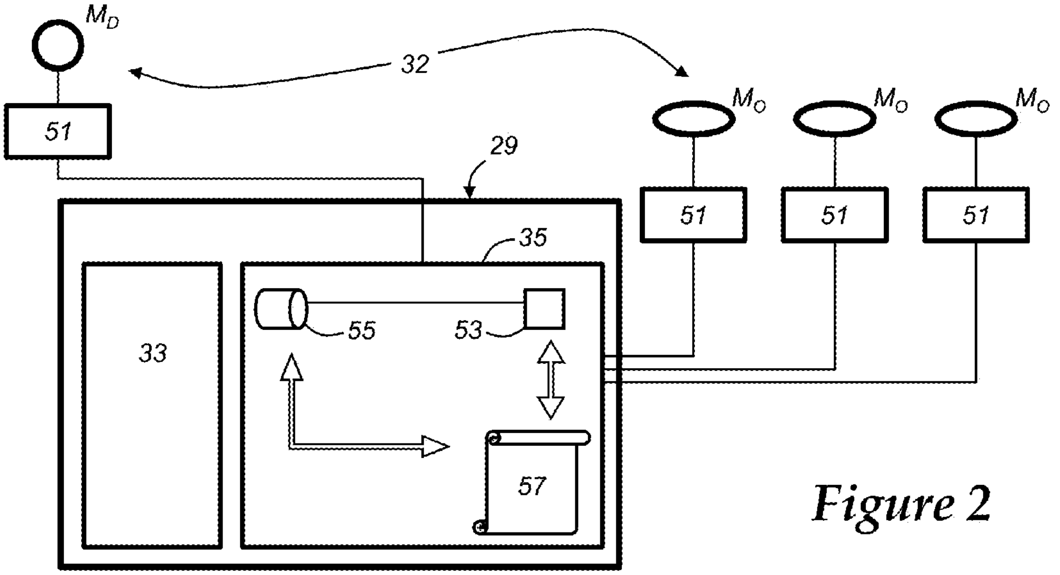
FIG. 2 is a schematic diagram of a vehicle audio quality system for suppressing sudden cabin noise.

The audio quality system 29 further comprises an on-board automated voice processing unit (VPU) 33 and a noise cancellation module (NCM) 35 which may be part of the telematics unit 30, as shown in FIGS. 1 and 2; however, this is not required. For example, the system 29 may be a separate component or device. For example, in one embodiment, the telematics unit 30 and/or VPU 33 are coupled to or are part of a vehicle head unit or infotainment unit. The VPU 33 may utilize human-machine interface (HMI) technology and may or may not apply automatic speech recognition (ASR) techniques; regardless, VPU hardware and techniques for using such devices are known. VPU 33 may be coupled to the noise cancellation module 35 which may suitably apply various acoustic techniques, software techniques, or both to speech audio and/or other similar desired audio in order to provide improved audio quality of an electronic (e.g., wireless) transmission. Acoustic techniques include: array mixing, dual channel off-axis mixing, and cross-correlation, just to name a few examples. And software techniques include: noise reduction, wind rejection, equalization, low frequency pre-emphasizing, and high frequency pre-emphasizing, just to name a few examples. Skilled artisans will appreciate other suitable acoustic and software techniques.

The arrangement of microphones 32 provides audio input to the telematics unit (e.g., more specifically the audio quality system 29) to enable the driver or other occupant to provide voice commands and carry out hands-free calling via the wireless carrier system 14 and/or via a SRWC link. The arrangement of microphones 32 may be heterogenous; i.e., the arrangement may include both directional microphones ($M_D$) and omni-directional microphones ($M_O$). As will be appreciated by skilled artisans, omni-directional microphones generally have a three-dimensionally spherical response; i.e., they are responsive in all directions. As used herein and as will be appreciated by skilled artisans, directional microphones are responsive in something less than all directions. Thus, directional microphones include: uni-directional microphones (e.g., cardioid), bi-directional microphones, and shot-gun or other multi-lobal microphones. However, these are merely examples; other implementations also may exist.

In some implementations, the arrangement of microphones includes both primary or hands-free audio (HFA) microphones 37 which may include directional or omni-directional microphones and secondary or active noise cancellation (ANC) microphones 39 which are generally omni-directional microphones. For example, FIG. 3A illustrates both—having one HFA microphone 37 in an A-pillar of the vehicle 12 and two ANC microphones in a headliner 41 of a vehicle cabin 43.

FIG. 3B illustrates that the arrangement of microphones 32 may be positioned in various patterns or configurations with respect to the headliner 41 and a centerline C of the vehicle 12. For example, position $m_1$ and position $m_7$ are positioned at first or far outboard locations (e.g., which may be at or near vehicle trim, grab handles, etc. adjacent the headliner 41). Or for example, positions $m_2$ and $m_6$ are at second outboard locations; i.e., spaced slightly closer to the centerline C but still more outboard than inboard. And for example, positions $m_3$ and $m_5$ are generally at inboard locations; i.e., relatively close or closer to the centerline C. And $m_4$ is positioned on the centerline C. These positions may be at any suitable longitudinal position of the vehicle. In at least some implementations, the longitudinal positions correspond to vehicle occupant seating. Moreover, some positions on the headliner 41 may be in an overhead console 45 (see FIGS. 4-9); e.g., particularly, positions $m_3$, $m_4$, and/or $m_5$. These relative positions may vary based upon the type of vehicle 12, various features of the cabin 43, vehicle seat positions, etc. Also, these relative positions are intended to be non-limiting; i.e., other headliner 41 positions also exist—e.g., more or less inboard or outboard. Furthermore, as illustrated in FIG. 3A, not all microphone positions need be in the headliner—e.g., some may be in one of the pillars (e.g., the A-, B-, C-, D-pillars), an instrument panel, or other suitable location.

FIGS. 4-9 illustrate various embodiments of the microphone arrangement 32. These are merely examples as well. For example, FIG. 4 illustrates one HFA microphone 37 at or near the vehicle centerline C (longitudinally positioned relative to the front seats) and an array of ANC microphones 39—two at the first outboard positions (longitudinally positioned relative to the front seats) and one at or near the centerline C (longitudinally positioned relative to the rear seats).

Figure 5:
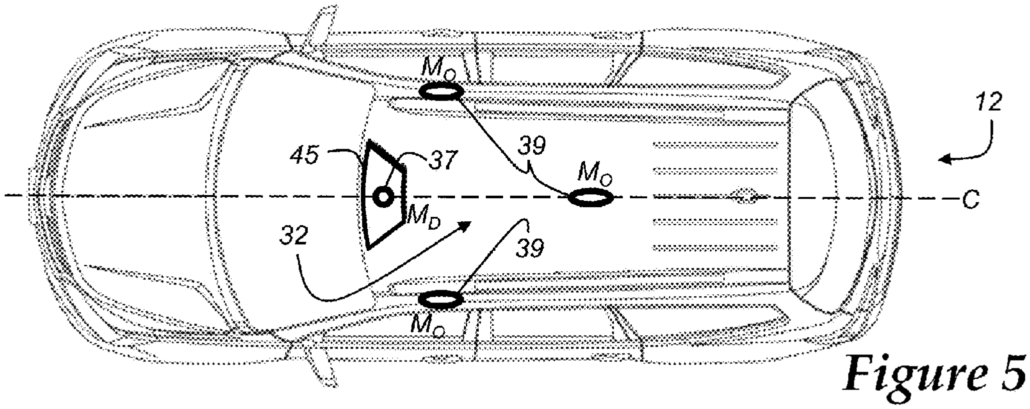

FIG. 5 illustrates one HFA microphone 37 at or near the vehicle centerline C carried by the overhead console 45 and an array of ANC microphones 39—similarly positioned as those described with respect to FIG. 4.

Figure 6:
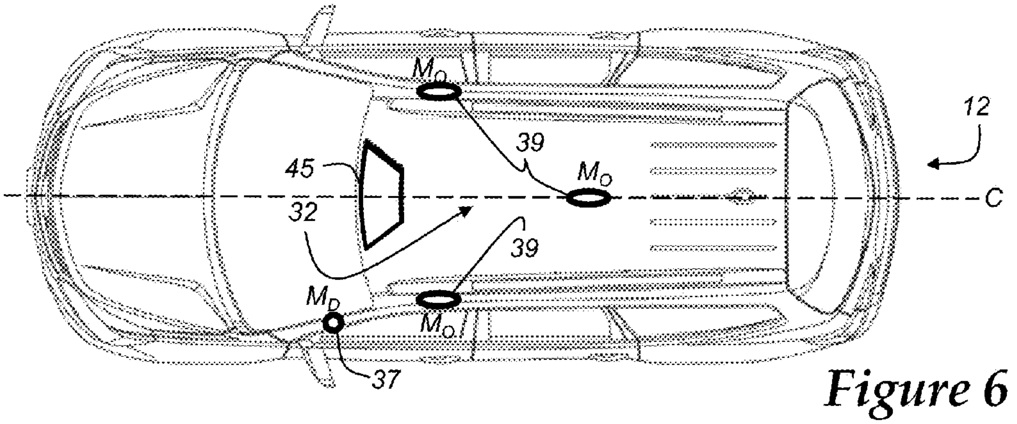

FIG. 6 illustrates one HFA microphone 37 in the driver's side A-pillar and an array of ANC microphones 39—similarly positioned as those described with respect to FIG. 4.

Figure 7:
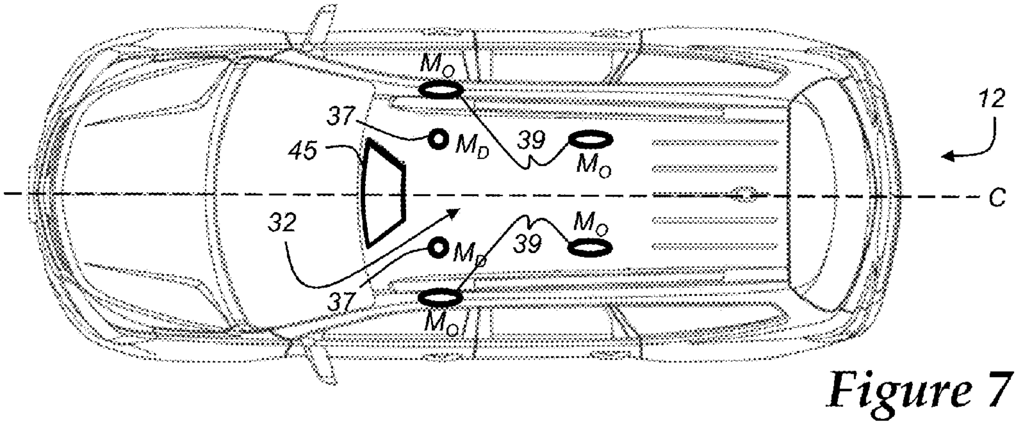

FIG. 7 illustrates two HFA microphones 37 at or near the second outboard positions (longitudinally positioned relative to the front seats) and an array of ANC microphones 39—two at the first outboard positions (longitudinally positioned relative to the front seats) and two at or near second outboard positions (longitudinally positioned relative to the rear seats).

Figure 8:
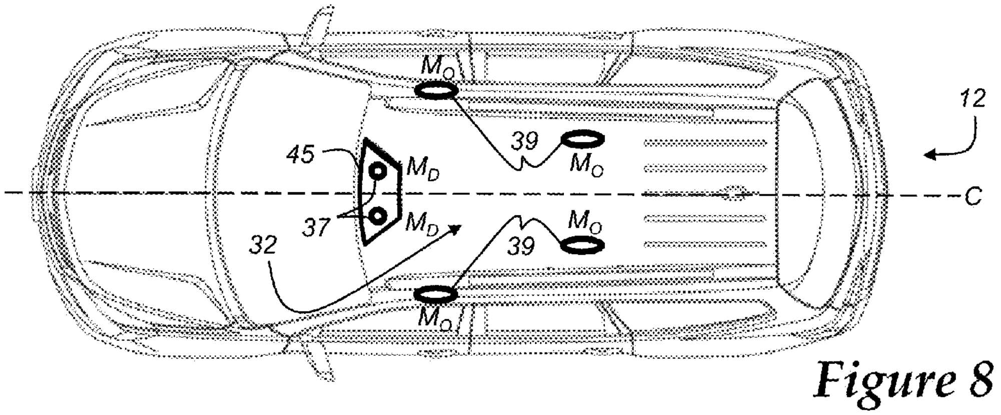

FIG. 8 illustrates two HFA microphones 37 at or near the vehicle centerline C carried by the overhead console 45 and an array of ANC microphones 39—similarly positioned as those described with respect to FIG. 7.

Figure 9:
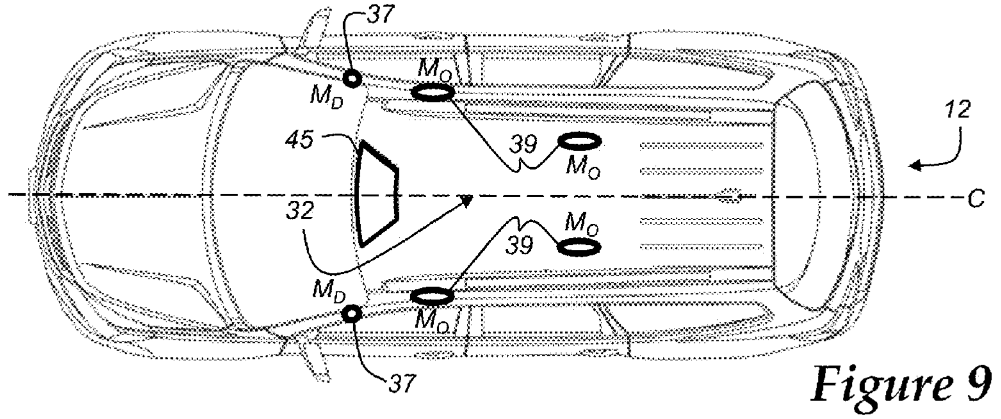

FIG. 9 illustrates two HFA microphones 37 in the driver's side and passenger-side A-pillars and an array of ANC microphones 39—similarly positioned as those described with respect to FIG. 7.

FIG. 2 illustrates that the NCM 35 of the audio quality system 29 is electrically coupled to the arrangement of microphones 32 and configured to receive inputs from each microphone. FIG. 2 illustrates that a preprocessor 51 optionally may be coupled between each microphone and the NCM 35; the preprocessors 51 may amplify, filter, buffer, and/or utilize other preprocessing techniques known to skilled artisans to prepare an audio signal for the VPU 33. In the illustration, one HFA microphone ($M_D$) is shown and three ANC microphones ($M_O$) by way of example only. The NCM 35 may further comprise a controller 53 electrically coupled to memory 55, and both the controller 53 and memory 55 may be capable of interacting with a software application 57. The memory 55 may include any non-transitory computer readable medium; it may store the application software as well as other data (in permanent or temporary memory).

The controller 53 may be configured to improve the quality of cabin audio that is desirable for wireless transmission. As will be explained in greater detail below, the controller 53 may execute these and other procedural steps: receive desired cabin audio input via the HFA microphone(s) 37; receive supplemental audio input via the array of ANC microphones 39 where the supplemental audio input includes a sudden cabin noise; and the apply a suppression procedure in response to the sudden cabin noise.

In one implementation, the NCM 35 is a separate module (as illustrated in FIG. 2); and in another implementation, the NCM 35 (including the controller 53 and memory 55) are part of the telematics unit 30. And in one particular instance, the controller 53 is the same device as the processor 52; similarly the memory 55 is the same device as the memory 54. FIGS. 2-9 are merely illustrative; other embodiments exist. Further, the VPU 33, NCM 35, and microphone arrangement 32 are merely a few of the vehicle electronics 28.

For example, other vehicle electronics 28 such as the pushbutton(s) 34 allow manual user input into the telematics unit 30 to initiate wireless telephone calls and provide other data, response, or control input. Separate pushbuttons can be used for initiating emergency calls versus regular service assistance calls to the call center 20. Audio system 36 provides audio output to a vehicle occupant and can be a dedicated, stand-alone system or part of the primary vehicle audio system. According to the particular embodiment shown here, audio system 36 is operatively coupled to both vehicle bus 44 and entertainment bus 46 and can provide AM, FM and satellite radio, CD, DVD and other multimedia functionality. This functionality can be provided in conjunction with or independent of the infotainment module described above. Visual display 38 is preferably a graphics display, such as a touch screen on the instrument panel or a heads-up display reflected off of the windshield, and can be used to provide a multitude of input and output functions. Various other vehicle user interfaces can also be utilized, as the interfaces of FIG. 1 are only an example of one particular implementation.

Wireless carrier system 14 is preferably a cellular telephone system that includes a plurality of cell towers 70 (only one shown), one or more mobile switching centers (MSCs) 72, as well as any other networking components required to connect wireless carrier system 14 with land network 16. Each cell tower 70 includes sending and receiving antennas and a base station, with the base stations from different cell towers being connected to the MSC 72 either directly or via intermediary equipment such as a base station controller. Cellular system 14 can implement any suitable communications technology, including for example, analog technologies such as AMPS, or the newer digital technologies such as CDMA (e.g., CDMA2000) or GSM/GPRS. As will be appreciated by those skilled in the art, various cell tower/base station/MSC arrangements are possible and could be used with wireless system 14. For instance, the base station and cell tower could be co-located at the same site or they could be remotely located from one another, each base station could be responsible for a single cell tower or a single base station could service various cell towers, and various base stations could be coupled to a single MSC, to name but a few of the possible arrangements.

Apart from using wireless carrier system 14, a different wireless carrier system in the form of satellite communication can be used to provide uni-directional or bi-directional communication with the vehicle. This can be done using one or more communication satellites 62 and an uplink transmitting station 64. Uni-directional communication can be, for example, satellite radio services, wherein programming content (news, music, etc.) is received by transmitting station 64, packaged for upload, and then sent to the satellite 62, which broadcasts the programming to subscribers. Bi-directional communication can be, for example, satellite telephony services using satellite 62 to relay telephone communications between the vehicle 12 and station 64. If used, this satellite telephony can be utilized either in addition to or in lieu of wireless carrier system 14.

Land network 16 may be a conventional land-based telecommunications network that is connected to one or more landline telephones and connects wireless carrier system 14 to call center 20. For example, land network 16 may include a public switched telephone network (PSTN) such as that used to provide hardwired telephony, packet-switched data communications, and the Internet infrastructure. One or more segments of land network 16 could be implemented through the use of a standard wired network, a fiber or other optical network, a cable network, power lines, other wireless networks such as wireless local area networks (WLANs), or networks providing broadband wireless access (BWA), or any combination thereof. Furthermore, call center 20 need not be connected via land network 16, but could include wireless telephony equipment so that it can communicate directly with a wireless network, such as wireless carrier system 14.

Computer 18 can be one of a number of computers accessible via a private or public network such as the Internet. Each such computer 18 can be used for one or more purposes, such as a web server accessible by the vehicle via telematics unit 30 and wireless carrier 14. Other such accessible computers 18 can be, for example: a service center computer where diagnostic information and other vehicle data can be uploaded from the vehicle via the telematics unit 30; a client computer used by the vehicle owner or other subscriber for such purposes as accessing or receiving vehicle data or to setting up or configuring subscriber preferences or controlling vehicle functions; or a third party repository to or from which vehicle data or other information is provided, whether by communicating with the vehicle 12 or call center 20, or both. A computer 18 can also be used for providing Internet connectivity such as DNS services or as a network address server that uses DHCP or other suitable protocol to assign an IP address to the vehicle 12.

Call center 20 is designed to provide the vehicle electronics 28 with a number of different system back-end functions and, according to the exemplary embodiment shown here, generally includes one or more switches 80, servers 82, databases 84, live advisors 86, as well as an automated voice response system (VRS) 88, all of which are known in the art. These various call center components are preferably coupled to one another via a wired or wireless local area network 90. Switch 80, which can be a private branch exchange (PBX) switch, routes incoming signals so that voice transmissions are usually sent to either the live adviser 86 by regular phone or to the automated voice response system 88 using VoIP. The live advisor phone can also use VoIP as indicated by the broken line in FIG. 1. VoIP and other data communication through the switch 80 is implemented via a modem (not shown) connected between the switch 80 and network 90. Data transmissions are passed via the modem to server 82 and/or database 84. Database 84 can store account information such as subscriber authentication information, vehicle identifiers, profile records, behavioral patterns, and other pertinent subscriber information. Data transmissions may also be conducted by wireless systems, such as 802.11x, GPRS, and the like. Although the illustrated embodiment has been described as it would be used in conjunction with a manned call center 20 using live advisor 86, it will be appreciated that the call center can instead utilize VRS 88 as an automated advisor or, a combination of VRS 88 and the live advisor 86 can be used.

The operating environment may further include one or more other vehicles (e.g., similar to vehicle 12 having telematics capability) and/or one or more mobile devices 96. Generally, the mobile device may be an electronic device which may be used to make mobile telephone calls across a wide geographic area where transmissions are facilitated by the wireless carrier system 14 (i.e., when the mobile device is connected to the wireless carrier system); but of course, this is merely an example. Other examples include short-range wireless communication e.g., via Bluetooth, Wi-Fi, Wi-Fi Direct, etc. Non-limiting examples of the mobile device 96 include a cellular telephone, a personal digital assistant (PDA), a Smart phone, a personal laptop computer or tablet computer having two-way communication capabilities, a netbook computer, a notebook computer, or any suitable combinations thereof. It should be appreciated that the mobile device 96 may communicate (e.g., transmit/receive) wirelessly with telematics unit 30 via cellular communication, a SRWC link, or both.

Method—

Figure 10:
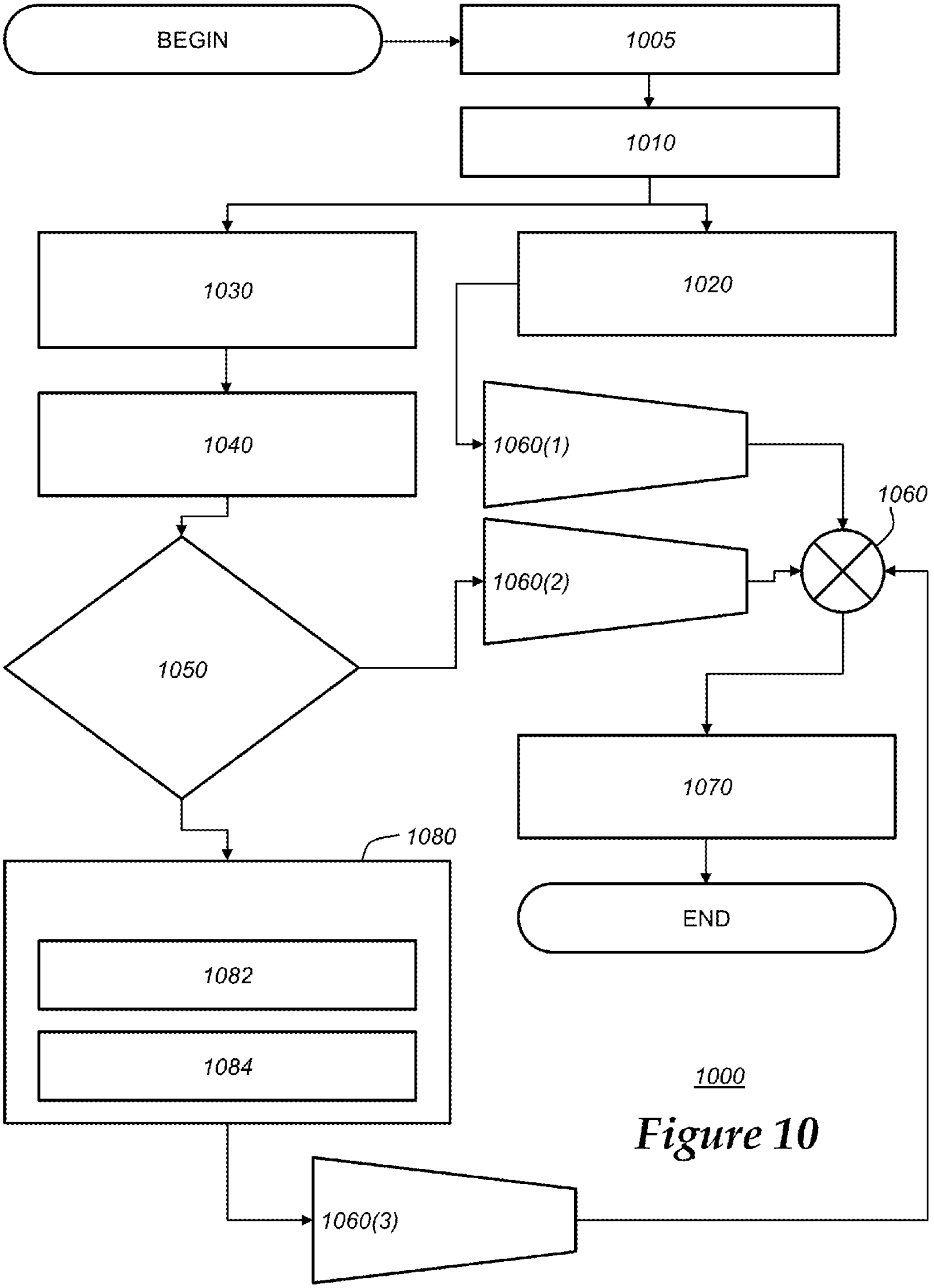
FIG. 10 is a flow diagram illustrating one method of using the microphone arrangements shown in FIGS. 4-9.

Turning now to FIG. 10, there is a flow diagram illustrating one embodiment of a method for suppressing sudden cabin noise during a hands-free audio microphone use. The method 1000 shown suppresses a sudden cabin noise received by the microphone arrangement 32 which is provided at step 1005. Providing the microphone arrangement may include installation or assembly into the vehicle 12 during the manufacturing process or after-market. In at least one embodiment, the providing step occurs during vehicle manufacture and assembly.

In step 1010, a wireless connection (e.g., a phone call) between a vehicle user (e.g., the driver or passenger) and another (or recipient) party is established. As will be appreciated by skilled artisans, the wireless connection may be facilitated by the vehicle's telematics unit 30, vehicle electronics 28, and the wireless communication system 14. The recipient party may be using another telematics-equipped vehicle, using mobile device 96, using a landline telephone, or any other suitable device. Furthermore, embodiments of the wireless connection include those by cellular transmission or via a short-range wireless communication link. Moreover, the wireless connection should be construed broadly enough to include voice calls or data calls.

During the wireless connection of step 1010, the microphone arrangement 32 receives cabin audio. More specifically, in step 1020, the microphone arrangement 32 receives desired audio input at one or more HFA microphones 37 so that the vehicle user's hands may be free to operate the vehicle 12. The desired audio input may include vehicle user speech or any other various sounds or tones which the user desires to transmit via the wireless connection. For example, in view of the embodiments illustrated in FIGS. 4-9, the driver, front seat passenger, or both may utter the desired audio. The HFA microphone(s) may receive this audio input and provide it to the VPU 33 and/or NCM 33.

In step 1030, the ANC microphones 39 may receive supplementary audio inputs while the desire audio inputs are received. According to the method 1000, the supplementary audio includes a sudden cabin noise input that occurs during the desired audio input. The sudden cabin noise input may have a magnitude sufficient to be heard include by the recipient party and be disruptive (e.g., it may be greater than 6 decibels and have a duration less than 16 milliseconds). Examples of sudden cabin noises include: weather-related noises (e.g., the beginning of a hard rain or hail, thunder, etc.), vehicle-related noises (e.g., the initial opening of a window at higher vehicle speeds or rapidly turning up a vehicle sound system, screeching tires, passing emergency vehicle sirens, etc.), and user-related noises (e.g., sneezing, coughing, electronic games, toys, screaming infants or children, etc.). These are merely examples of sudden cabin noise; the foregoing is intended to be a non-limiting list of examples and is by no means exhaustive.

Conventional noise reduction systems will mix the sudden cabin noise input with the desired audio resulting in sudden cabin noise being wirelessly transmitted to the recipient party. This may be undesirable to the user. After receiving both the desired audio input and the supplementary audio input (which includes the sudden cabin noise input), the method proceeds to step 1040.

In step 1040, the method 1000 applies a noise suppression procedure—more specifically, a first suppression procedure. The first suppression procedure may include using noise suppression techniques such as known acoustic techniques and known software techniques. Nonlimiting examples of acoustic techniques include array mixing, dual channel off-axis mixing, and cross-correlation. And nonlimiting examples of software techniques include wind rejection, equalization, low frequency pre-emphasizing, and high frequency pre-emphasizing. These listings are merely examples again—other techniques will be appreciated by skilled artisans.

Following step 1040, the method determines whether the first suppression procedure adequately suppressed the sudden cabin noise (step 1050); i.e., was the sudden cabin noise portion of the total audio signal adequately attenuated. According to one embodiment, step 1050 determines whether the sudden cabin noise was normalized. As used herein, normalization is the scaling down of the noise components or portions from each the microphones 37, 39 in the arrangement 32 to a common level; i.e., the noise component(s) of the desired audio and supplemental audio inputs. If, after the first suppression procedure, the sudden cabin noise input is not lowered to a level common with the other noise inputs, the method proceeds to step 1080, and if normalization was achieved, the method proceeds to step 1060.

In step 1060, the method 1000 accepts all audio inputs from the microphone arrangement 32 (i.e., the desired audio input 1060(1) and the supplementary audio inputs 1060(2)) and mixes the audio.

Following mixing step 1060, a total audio signal may be further processed (if desired) and wirelessly transmitted using the telematics unit 30 (step 1070). In this scenario, the method 1000 ends.

Where normalization was not achieved in step 1050, the method proceeds to step 1080 where a second suppression procedure is applied. Step 1080 is illustrated as having substeps 1082 and 1084. In sub-step 1082, the method identifies at least one object microphone. The object microphone may be one of the ANC microphones 39 and may be the particular microphone 39 which received the sudden cabin noise input with the greatest magnitude. This identification may occur in a number of ways; e.g., in one example, the sudden cabin noise may be associated or correlated with a spike or transient noise component in each of the supplementary audio inputs. These spikes may be compared with one another and the greatest magnitude may be determined.

In sub-step 1084 which follows sub-step 1082, the method may cancel or eliminate the supplementary audio input from the object microphone. This may include canceling all or a portion of the supplementary audio input from the object microphone—e.g., at least canceling a window of supplementary audio surrounding the sudden noise input. In one example, the window that is canceled is at least twice the duration of the spike (e.g., if the audio spike's duration is 8 milliseconds (ms), a cancellation window is 16 ms).

Following sub-step 1084, the remaining supplementary audio inputs (i.e., audio inputs from each microphone 39 except the object microphone) are sent to the mixer again. This time, following sub-step 1084, step 1060 includes accepting and mixing the desired audio input 1060(1) and the remaining supplementary audio inputs 1060(3); i.e., excluding the object microphone's audio input. Thereafter, the total audio signal is output and the method proceeds to step 1070 as previously described.

It should be appreciated that other embodiments also exist. For example, the HFA microphones 37 shown in FIGS. 4-9 were all illustrated as directional microphones; however, this is not required—e.g., one or more of these HFA microphones may be omni-directional microphones. Or for example, one or more of the ANC microphones 39 may be directional microphones.

In other embodiments, the microphone arrangements 32 shown in FIGS. 4-9 may differ. For example, there may be more than two HFA microphones or more than four ANC microphones. Further, the positioning of the microphones may differ—being more or less inboard or outboard of the vehicle's centerline.

In another embodiment, more than one microphone is identified as the object microphone and the audio inputs from those identified object microphones are canceled. For example, the identified object microphones are those associated with the largest magnitude spikes.

Thus, there has been described a vehicle audio quality system for suppressing sudden cabin noise while a vehicle occupant is using a microphone arrangement for receiving voice and other suitable audio. The system receives various audio inputs that include a sudden cabin noise. When this sudden cabin noise occurs, the system applies various noise suppression procedures to attenuate the sudden cabin noise. If necessary, the system is capable of identifying and eliminating the audio input of one or more of the microphone inputs that received the sudden noise input with the greatest magnitude.

It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "e.g.," "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A method of sudden cabin noise suppression for a vehicle, comprising the steps of:

providing an arrangement of heterogeneous microphones in the vehicle, the arrangement comprising a hands-free audio (HFA) microphone and an array of secondary microphones, wherein the arrangement includes at least one directional microphone and at least one omni-directional microphone;

receiving a desired audio input via the HFA microphone;

while receiving the desired audio input, receiving supplemental audio inputs via the array of secondary microphones, wherein the supplemental audio inputs include a sudden cabin noise input;

applying a first suppression procedure to the sudden cabin noise input; and when the first suppression procedure does not normalize the sudden cabin noise input, then applying a second suppression procedure.

2. A method of sudden cabin noise suppression for a vehicle, comprising the steps of:

providing an arrangement of microphones in the vehicle, the arrangement comprising a hands-free audio (HFA) microphone and an array of active-noise canceling (ANC) microphones;

receiving a desired audio input via the HFA microphone;

while receiving the desired audio input, receiving supplemental audio inputs via the array of ANC microphones, wherein the supplemental audio inputs include a sudden cabin noise input;

applying a first suppression procedure to the sudden cabin noise input; and when the first suppression procedure does not normalize the sudden cabin noise input, then applying a second suppression procedure.

3. The method of claim 2, wherein the ANC microphones are omni-directional microphones.

4. The method of claim 3, wherein the HFA microphone is an omni-directional microphone or a directional microphone.

5. The method of claim 4, wherein the HFA microphone is the directional microphone.

6. The method of claim 2, wherein the providing step includes providing a plurality of HFA microphones for receiving the desired audio input.

7. The method of claim 2, wherein the first suppression procedure includes using one or more suppression techniques including: array mixing, dual channel off-axis mixing, cross-correlation, noise reduction, wind rejection, equalization, low frequency pre-emphasizing, and high frequency pre-emphasizing.

8. The method of claim 2, further comprising: mixing the desired audio input with the supplemental audio input to prepare a total audio signal to be prepared for wireless transmission.

9. The method of claim 8, wherein the second suppression procedure includes:

identifying an object microphone from among the array of ANC microphones, wherein the object microphone receives the sudden cabin noise input with the greatest magnitude; and prior to the mixing step, canceling the supplemental audio input associated with the object microphone.

10. The method of claim 2, wherein the arrangement of microphones includes one or more HFA microphones located in one or more of the following vehicle cabin locations: centered in a vehicle headliner, at an inboard region of the vehicle headliner, in an overhead console of the vehicle headliner, or in an A-pillar of the vehicle.

11. The method of claim 10, wherein the arrangement of microphones includes two ANC microphones located in one or more of the following vehicle cabin locations: centered in a vehicle headliner, at an inboard region of the vehicle headliner, or at an outboard region of the vehicle headliner.

12. The method of claim 2, wherein the desired audio input includes user speech.

13. A vehicle audio quality system for suppressing sudden vehicle cabin noise, comprising:

an arrangement of heterogeneous microphones comprising:

a first microphone;

a plurality of secondary microphones, and a noise cancellation module (NCM) comprising a controller and a non-transitory computer-readable medium for storing application software executable by the controller to improve the quality of desired cabin audio received by the first microphone, the software performing the steps of:

receiving a desired audio input from the first microphone;

receiving supplemental audio input via the plurality of secondary microphones that includes a sudden cabin noise input; and applying a suppression procedure to the sudden cabin noise input.

14. The system of claim 13, wherein the suppression procedure includes a first suppression procedure that includes acoustic techniques, software techniques, or both used to normalize the sudden cabin noise input, and a second suppression procedure applied when the first suppression procedure fails to normalize the sudden cabin noise input.

15. The system of claim 14, wherein the second suppression procedure includes:

identifying an object microphone from among the array of secondary microphones, the object microphone receiving the sudden cabin noise input at a greatest magnitude; and canceling the supplemental audio input from the object microphone.

16. The system of claim 15, further comprising: mixing the desired audio input and the supplemental audio input together for wireless transmission, wherein the mixing step excludes the supplemental audio input associated with the object microphone.

17. The system of claim 13, further comprising a plurality of first microphones.

18. The system of claim 13, wherein the first microphone is a directional microphone, wherein the plurality of secondary microphones include at least one omni-directional microphone.

* * * * *